United States Patent [19]

Levy

[11] Patent Number: 5,064,821

[45] Date of Patent: Nov. 12, 1991

[54] METHOD AND COMPOSITIONS FOR OVERCOMING TETRACYCLINE RESISTANCE WITHIN LIVING CELLS

[75] Inventor: Stuart B. Levy, Boston, Mass.

[73] Assignee: Trustees of Tufts College, Medford, Mass.

[21] Appl. No.: 484,904

[22] Filed: Feb. 26, 1990

Related U.S. Application Data

[63] Continuation-in-part of Ser. No. 850,843, Apr. 11, 1986, Pat. No. 5,021,407, which is a continuation of Ser. No. 442,688, Nov. 18, 1982, Pat. No. 4,806,529.

[51] Int. Cl.$^5$ .................... A01N 37/18; A61K 35/00
[52] U.S. Cl. .................................. 514/154; 424/114
[58] Field of Search ................. 514/154; 424/114

[56] References Cited

U.S. PATENT DOCUMENTS

| | | | |
|---|---|---|---|
| 3,236,736 | 2/1966 | Fitch et al. | 514/154 |
| 3,454,697 | 7/1969 | Joyner et al. | 514/154 |
| 3,863,009 | 1/1975 | Johnston | 514/154 |

*Primary Examiner*—Stanley J. Friedman
*Assistant Examiner*—T. Criares
*Attorney, Agent, or Firm*—David Prashker

[57] ABSTRACT

The present invention provides an improved methodology by which therapeutically to overcome resistance to tetracycline in living cells including bacteria, parasites, fungi, and rickettsiae. The methodology employs 13-(substituted mercapto) derivatives of tetracycline in combination with other tetracycline-type antibiotics as a synergistic combination of compositions to be administered simultaneously or concurrently. The concomitantly administered compositions effectively overcome the tetracycline resistant mechanisms present such that the cell is effectively converted from a tetracycline-resistant state to a tetracycline-sensitive state. The combination also effects a synergistic bacteriocidal activity against susceptible and resistant cells.

13 Claims, No Drawings

METHOD AND COMPOSITIONS FOR OVERCOMING TETRACYCLINE RESISTANCE WITHIN LIVING CELLS

CROSS-REFERENCE

This application is a continuation-in-part of application Ser. No. 850,843 filed Apr. 11, 1986, now U.S. Pat. No. 5,021,407 issued June 4, 1991, which was a continuation of application Ser. No. 442,688 filed Nov. 18, 1982, now U.S. Pat. No. 4,806,529 issued Feb. 21, 1989.

RESEARCH SUPPORT

The research for the present invention was supported by funds through Tufts University.

FIELD OF THE INVENTION

The present invention is concerned generally with therapeutic tetracycline treatment of living cells; and is particularly directed to methods and materials for altering and overcoming resistance to tetracycline within microorganisms such as bacteria, fungi, rickettsia, and the like.

BACKGROUND OF THE INVENTION

The development of the tetracycline antibiotics was the direct result of a systematic screening of soil specimens collected from many parts of the world for evidence of microorganisms capable of producing bacteriocidal and/or bacteriostatic compositions. The first of these novel compounds was introduced in 1948 under the name chlortetracycline. Two years later oxytetracycline became available. The detailed elucidation of the chemical structure of these agents confirmed their similarity and furnished the analytical basis for the production of a third member of this group in 1952, tetracycline. By 1957, a new family of tetracycline compositions characterized chemically by the absence of the ring-attached $CH_3$ group present in the earlier compositions was prepared and became publically available in 1959 under the official name demeclocycline. Subsequently, methacycline, a derivative of oxytetracycline, was introduced in 1966; doxycycline became available by 1967; and minocycline was in use by 1972. For clarity, for general ease of understanding, and for comparison purposes, these individual tetracycline type agents are structurally compared within Table I below.

TABLE I
TETRACYCLINE

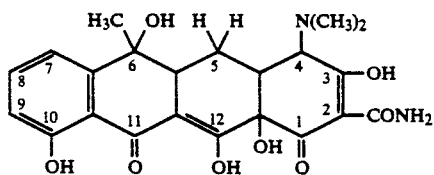

| Congener | Substituent(s) | At Carbon Position Nos. |
|---|---|---|
| Chlorotetracycline | —Cl | (7) |
| Oxytetracycline | —OH, —H | (5) |
| Demeclocycline | —OH, —H; —Cl | (6;7) |
| Methacycline | —OH, —H; =$CH_2$ | (5;6) |
| Doxycycline | —OH, —H; —$CH_3$, —H | (5;6) |
| Minocycline | —H, —H; —N($CH_3$)$_2$ | (6;7) |

Subsequent to these initial developments, much research effort was focused on developing new tetracycline antibiotic compositions effective under varying therapeutic conditions and routes of administration; and for developing new tetracycline analogues which might prove to be equal or more effective than the originally introduced tetracycline families beginning in 1948. Representative of such developments are U.S. Pat. Nos. 3,957,980; 3,674,859; 2,980,584; 2,990,331; 3,062,717; 3,557,280; 4,018,889; 4,024,272; 4,126,680; 3,454,697; and 3,165,531. It will be understood that these issued patents are merely representative of the range of diversity of investigations seeking tetracycline and tetracycline analogue compositions which are pharmacologically active.

Historically, soon after their initial development and introduction, the tetracyclines regardless of specific formulation or chemical structure were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in-vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic—as for example Pneumococci and Salmonella. The rise of tetracycline-resistant organisms has led not only to a general decline and avoidance of tetracyclines and tetracycline analogue compositions as antibiotics of choice but has also launched major efforts and investigations to uncover the mechanism for tetracycline resistance—in the hope that some effective means might be developed to overcome the problem of tetracycline-resistance and thus reestablish the pharmacological value and efficacy of tetracyclines as a whole.

The following represents a current summary of the investigations and knowledge regarding the mechanism of action for tetracyclines in bacteria. The site of action for tetracyclines is the bacterial ribosome; and that at least two different processes appear to be required for tetracyclines to gain access to the cytoplasm and the ribosomes of bacteria. The first process is a passive diffusion of the tetracycline through hydrophilic pores located in the outer cell membrane. One of these structures is the major outer membrane protein, Omp F. The second process involves an energy-dependent active transport system that pumps all tetracyclines through the inner cytoplasmic membrane. In the tetracyline-sensitive cell or organism, once the tetracycline gains access to the interior of the cell, it is able to bind to the ribosomes and to inhibit protein synthesis. However, in many tetracycline resistant cells and organisms, an efflux pump system is present which appears to bind the tetracycline molecule and actively transports the tetracycline molecule out of the organism into the surrounding environment. This active efflux employs an inner membrane protein designated TET (or Tet) protein which is synthesized in the cell from a gene which is generally acquired by the organism. Often the gene is present on an extra-chromosomal, autonomously replicating plasmid or a transposon.

Tetracycline resistance is often regulated—that is, inducible by tetracycline. Investigations of active tetracycline efflux systems and the details of the active efflux mechanism of action have been well documented and include the following publications, each of which is expressly incorporated by reference herein: Chopra et al., *J. Antimicrobiol. Chemotherapy* 8:5-21 (1981); Levy and McMurry, *Biochem. Biophys. Res. Comm.* 56:1060-1068 (1974); Levy and McMurry, *Nature* 275:90-92 (1978); McMurry and Levy, *Antimicrobial Agents And Chemotherapy* 114:201-209 (1978); McMurry et al., *Proc. Nat. Acad. Sci. U.S.A.* 77:3974-3977 (1980); Ball et al., *Biochem. Biophys. Res. Comm.* 93:74-81 (1980); Curiale and Levy, *J. Bact.* 151:209-2115 (1982); Mendez et al., *Plasmid* 3:99-108 (1980); Curiale et al., *J. Bact.* 157:211-217 (1984); and Levy, S. B., *Journal Of Antimicrobial Chemotherapy* 24:1-3 (1989).

In addition, a second mechanism of tetracycline resistance for cells is known and in effect. This resistance mechanism involves a cytoplasmic protein which protects the intracellular ribosomes from the inhibitory action of tetracyclines. This form of tetracycline resistance is described within Burdett, V., *J. Bact.* 165:564-569 (1986); and Levy, S. B., *J. Antimicrob. Chem.* 24:1-3 (1989).

With the increased understanding and knowledge regarding the origin and the mechanisms of tetracycline resistance in various cells and microorganisms, overt investigations and developments seeking means for overcoming these mechanisms, notably the active efflux system have been attempted. One successful approach is described within U.S. Pat. No. 4,806,529 issued Feb. 21, 1989—an innovation which is a precursor of more recent developments. Clearly, additional methods and materials for overcoming tetracycline-resistance in bacteria and other organisms is most desirable and needed. Substantive advances which additionally overcome the active efflux system for tetracycline in the resistant cell would be presently recognized by the ordinary practitioner in the art as a major asset and innovation.

SUMMARY OF THE INVENTION

The present invention provides methods for therapeutically treating a tetracycline-resistant cell and also provides a method for altering a cell from a tetracycline-resistant state into a tetracycline-sensitive state. This method comprises the steps of: administering to the cell a predetermined quantity of at least one composition selected from the chemical class consisting of 6-deoxy-13-(substituted mercapto)tetracyclines; concomitantly administering to the cell a predetermined quantity of at least one other composition selected from the chemical class consisting of tetracycline and tetracycline analogues which are not 6-deoxy-13-(substituted mercapto)tetracyclines; and allowing the cell to preferentially react with the administered 6-deoxy-13-(substituted mercapto)tetracycline composition.

The unique methodology is able to alter and to convert tetracycline-resistant cells or microorganisms into tetracycline-sensitive ones; and, accordingly, to provide a therapeutic treatment for those living subjects, human, animal, and plants which have been previously refractory to a tetracycline therapeutic regimen.

DETAILED DESCRIPTION OF THE PREFERRED EMBODIMENTS

The present invention represents a unique methodology by which to overcome the increasing resistance of many different varieties of cells and microorganisms to the antibiotic activity of tetracyclines, their analogues and derivatives. The present invention takes into account and acts upon the existence of specific DNA sequences, which are typically found on plasmids and transposons, and which specify proteins for tetracycline-resistant determinants. Some of these determinants act via an active efflux system which maintains an intracellular tetracycline concentration below those levels able to inhibit protein synthesis within the microorganism. Other determinants act by protecting the ribosome from binding with tetracycline. The present invention therefore represents a major advance and improvement in efficacious and reliable techniques for overcoming tetracycline resistance in living cells generally; and for reestablishing tetracyclines as an antibiotic of choice in the treatment of infectious diseases caused by the everincreasing variety and diversity of disease agents.

The Range And Variety Of Susceptible Tetracycline-Resistant Cells

The present invention is intended for use with any and all tetracycline-resistant cells or organisms which are found to contain or carry the genetic determinants responsible for tetracycline resistance and without regard to the mechanism of resistance. As described within the recent publication of Levy, S. B., *Journal Of Antimicrobial Chemotherapy* 24:1-3 (1989), the text of which is expressly incorporated by reference herein, more than a dozen different distinguishable tetracycline resistance determinants have been uncovered [Levy, S. B., "Resistance to the Tetracyclines," in *Antimicrobial Drug Resistance*, (Bryan, L. E., editor), Academic Press, Orlando, Fla., 1984, pages 191-204; Levy, S. B., *ASM News* 54:418-421 (1988)]. As these genetic determinants of these tetracycline-resistant cells have been elucidated, it has become generally accepted that the same or very similar genes are responsible for resistance in a large number of different aerobic and anaerobic microorganisms.

The present invention is therefore believed suitable for use with at least, but not exclusively, the following genera: Gram-negative genera, in particular Enterobacteriaceae, which harbor Class A-E tetracycline resistance determinants; Grampositive genera including streptococci, staphylococci, and bacillus species which bear the Class K and L tetracycline resistance determinants; aerobic and anaerobic microorganisms bearing the Class M, N, and O determinants represented by *Streptococcus agalactiae*, Enterococcus, Gardnarella and Neisseria species, Mycoplasma and Ureaplasma, and in Clostridium; *Clostridium perfringens* bearing the Class P tetracycline-resistant determinant; and the genera of Pseudomonas, Proteus, and other organisms whose tetracycline resistance determinants have not yet been specifically identified.

It will be recognized and appreciated that the above listed organisms are themselves only representative and illustrative of the range, variety, and diversity of cell types, bacterial species, fungi, parasites, and rickettsial disease agents which may be therapeutically treated using the present methodology. It will be expressly noted that no specific class, genus, species, or family of cell, microorganism, or parasite is excluded; to the contrary, it is expected that with future investigations into the determinants responsible for tetracyclne resistance, ever greater numbers of different cells will be recognized as suitable for efficacious treatment using the present invention. In addition, in view of the recent use of tetracyclines for treatment of neoplasms, it is deemed that the present methodology would be useful in such therapies [van der Bozert et al., *Cancer Res.* 48:6686–6690 (1988)].

The Steps Comprising The Present Methodology

The present methodology is a major improvement over presently known methods for dealing with tetracycline resistance within disease-causing cells and organisms. The methodology requires only three essential steps: the administration to the tetracycline-resistant cell of a predetermined quantity of at least one composition selected from the chemical class consisting of 6-deoxy-13-(substituted mercapto)tetracyclines; concurrently or simultaneously administering to the tetracycline-resistant cell a predetermined quantity of at least one other composition selected from the chemical class consisting of tetracyclines, its analogues and derivatives, which are not chemically formulated as 6-deoxy-13-(substituted mercapto)tetracyclines; and subsequently allowing the resistance mechanism of the cell to preferentially react with the administered 6-deoxy-13-(substituted mercapto)tetracycline composition and consequently avoid preferential reaction with the other administered composition which is the tetracycline, a tetracycline analogue or derivative composition.

Clearly therefore, it is recognized and understood that two different compositions are to be administered concurrently, sequentially, or simultaneously to the tetracycline-resistant cell. Moreover, it will be noted that the methodology requires and relies upon a preferential binding and reaction with the administered 6-deoxy-13-(substituted mercapto)tetracycline composition in-situ; and consequently demonstrate a substantial lack of attraction or preference for the other administered tetracycline composition, analogue, or derivative present in-situ. The operation, utility, and efficacy of the present methodology is thus based upon an empirically demonstratable preference of the tetracycline-resistant cell for one class of composition over another when both classes of composition are introduced concomitantly—that is, concurrently, sequentially, or simultaneously to the resistant cell.

To date, there is no basis, system, or technique which can be employed to accurately predict which of two similar tetracycline formulations and chemical structures would be preferentially reactive with the resistance systems of cells. Earlier investigations, as described within U.S. Pat. No. 4,806,529 issued Feb. 21, 1989, have demonstrated that tetracycline [i.e., 4-(Dimethylamino)-1,4,4a,5,5a,6-11,12a-octahydro-3,6,10,12,12a-pentahydroxy-6-methyl-1-11-dioxo-2-naphthacenecarboxanide] is not actively effluxed from the cell and consequently enters tetracycline-resistant cells when administered concurrently or simultaneously with other tetracycline analogues and derivatives such as minocycline or thiatetracycline. The present invention expands and improves upon these earlier investigations in substantial degree. It now provides the user with an improved class of 13-substituted mercapto tetracyclines which unexpectedly have been found to show the highest avidity for the mechanisms involved in tetracycline resistance, whether efflux system or ribosome protection based. The present methodology is therefore useful with all tetracycline-resistant cells regardless of the specific nature or mechanism present within that cell which provides for tetracycline resistance. On this basis of understanding, the different classes of tetracycline formulations and compositions will be described in detail.

Formulation, Structure, And Diversity Of 6-deoxy-13-(substituted mercapto)tetracyclines The 13 substituted mercapto tetracylines are conventionally known in the art as tetracyclines possessing antimicrobial activity in and of themselves against a variety of gram-positive bacteria. This class of tetracyclines, its conventionally recognized pharmacological activity, and methods for its synthesis are described within U.S. Pat. No. 3,165,531, the text of which is expressly incorporated by reference herein. This class is most broadly defined by Formula I below.

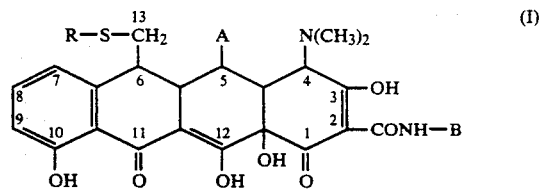

wherein

A is selected from the group consisting of hydrogen and a hydroxyl group;

B is selected from the group consisting of a hydrogen atom, a methylene group, and any linear, branched, or ring structure comprising from 1–6 carbon atoms and optionally including heteroatoms such as oxygen and nitrogen atoms; and R is selected from the group consisting of organic entities comprising from 1–12 carbon atoms, with or without other heteroatoms including sulfur, oxygen, halogen, nitrogen, and the like, and takes form as linear, branched, or cyclic alkyl, aryl, or alkylaryl structures.

The preferred compositions, as empirically demonstrated hereinafter, are S-substituted alkyl derivatives at the No. 13 carbon ranging from 1–10 carbon atoms in length. Nevertheless, it is expected that a wide variety of RCO, RCX where X is a halogen, RHC$_2$, and NRHC$_2$ analogue and derivative forms in linear, branched, or cyclic structural format would be useful and operative in the present methodology in varying degrees. Accordingly, all such embodiments are deemed to be within the scope of Formulation I above.

As representative examples of the preferred embodiments of this class which were empirically evaluated, some preferred 6-deoxy-13-(substituted mercapto)tetracyclines (hereinafter "13-S-Derivatives") and their respective blocking activities are provided within Table II below.

TABLE II

| BLOCKING ACTIVITY OF 13-S DERIVATIVES OF METHACYCLINE | | |
|---|---|---|
| 13-S-Derivatives | Number of Carbon Atoms | $K_i(ug/ml)^1$ |
| Decyl | 10 | 8.0 |
| Hexyl | 6 | 3.1 |
| Cyclohexyl | 6 | 0.4 |
| Benzyl | 7 | 0.9 |

TABLE II-continued
BLOCKING ACTIVITY OF 13-S DERIVATIVES OF METHACYCLINE

| 13-S-Derivatives | Number of Carbon Atoms | $K_i(ug/ml)$[1] |
|---|---|---|
| p-Cl-Benzyl | 7 | 1.5 |
| p-Me-Benzyl | 8 | 1.2 |
| Cyclopentyl | 5 | 0.2 |
| Butyl | 4 | 0.5 |
| t-Butyl | 4 | 0.3 |
| Isobutyl | 4 | 0.1 |
| Propyl | 3 | 0.4 |
| Isopropyl | 3 | 0.4 |
| Dihydroxypropyl | 3 | 3.9 |
| Ethyl | 2 | 0.4 |

[1] By everted membrane vesicle assay

From this representative listing, it will be noted that the shorter chain length substitutions or smaller adducts (cyclohexyl vs. hexyl; isobutyl vs. butyl; benzyl vs. parachlorobenzyl) are preferred inhibitors of the efflux system. These results lead to a general conclusion that the activity of compositions having substitutions at the 13th carbon relate more to the size of the molecule than to the charge despite the presence of the sulfur atom. The longer chain length substitutions at the 13th carbon atom (e.g., decyl and hexyl) are not as active as the shorter length substitutions (e.g., butyl, propyl, and ethyl). Furthermore, the dihydroxypropyl derivative behaves more poorly in the blocking assay than the propyl or isopropyl derivative forms. On this basis, therefore, it is expected that a most preferred composition would be one having mercapto-substitutions on the 13th carbon atom in which the elipsoidal volume of the substituent joined to the sulfur atom is in the approximate size range of that provided by the butyl, benzyl or cyclopentyl derivatized structures.

Moreover, the data of Table II indicate that the administration to a resistant cell of a 13-substituted mercaptan derivative or a composition which appears structurally similar to a 13-substituted mercaptan derivative would effectively block the resistance mechanism of the cell; and allow the concomitant administration of another tetracycline, tetracycline analogue, or tetracycline derivative to effectively inhibit further cell growth.

Formulation, Structure, And Range Of Other Tetracyclines, Tetracycline Analogues, And Tetracycline Derivative Forms The present invention requires that at least one other composition which is not chemically a 6-deoxy-13-(substituted mercapto)tetracycline be administered concurrently or simultaneously with the 13-S-derivative form to the cell. This additional administered composition is any "tetracycline-type antibiotic" currently known which includes tetracycline itself; or any member of the tetracycline family including all analogues and derivatives which are NOT 13-carbon substituted mercaptan compounds. Accordingly, the broadest definition for the additional tetracycline, analogue, or derivative to be administered concurrently is defined by Formula II below.

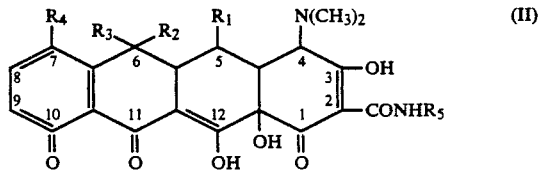

wherein $R_1$–$R_5$ may be a hydrogen atom, a halogen atom, a hydroxyl group, or any other organic composition comprising from 1–8 carbon atoms and optionally include a heteroatom such as nitrogen, oxygen, in linear, branched, or cyclic structural formats. A very wide range and diversity of embodiments within the definition of Formula II as are described within *Essentials Of Medicinal Chemistry*, John Wiley and Sons, Inc., 1976, pages 512–517, the text of which is expressly incorporated by reference herein. Preferably $R_1$ and $R_2$ are hydrogen or a hydroxyl group; $R_3$ is a hydrogen or a methyl group; $R_4$ is a hydrogen atom, a halogen, or a nitrogen containing entity; and $R_5$ is a hydrogen atom, or a nitrogen containing ring structure. The commonly known tetracycline analogues and derivatives include the following: oxytetracycline; chlortetracycline; demeclocycline; doxycycline; chelocardin; minocycline; rolitetracycline; lymecycline; sancycline; methacycline; apicycline; clomocycline; guamecycline; meglucycline; mepycycline; penimepicycline; pipacycline; etamocycline; and penimocycline. It will be recognized and appreciated that these specific tetracycline compositions (as well as many others conventionally known and available through the scientific literature or from commercial sources) may be employed as the alternative tetracycline-type composition which does not contain a 13-carbon substituted mercapto group as part of its formulation and chemical structure.

Modes Of Administration, Proportions, Dosages, And Other Variables

The individual compositions embodying Formula I, 13-S-derivatives, and Formula II, alternative tetracycline compounds, can be administered concurrently, sequentially, or simultaneously in any appropriate carrier for oral, topical, or parenteral administration. It is also possible that the two discrete compositions could be linked covalently or otherwise joined to each other and/or to other ligands. These compositions can be introduced by any means that affects an infectious or disease state caused by tetracycline-resistant microorganisms in humans and/or animals. The specific route of administration, the choice of carrying materials, and the particular means for introducing each composition concomitantly to the tetracycline-resistant cells are of no major importance or relevance.

Accordingly, if the 13-S-derivative composition and the other alternative tetracycline-type compound are to be applied topically, they can be individually or mutually admixed in a pharmacologically inert topical carrier such as a gel, an ointment, a lotion, or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as antioxidants, humectants, viscosity stabilizers, and the like may also be added if and when necessary.

Similarly, if the 13-S-derivative composition and the alternative tetracycline-type composition are to be introduced concurrently or simultaneously in parenteral form, each composition will be prepared individually or in combination in sterile form; in multiple or single dose formats; and be dispersed in a fluid carrier such a sterile physiological saline or 5% dextrose solutions commonly used with injectables.

Furthermore, if the present methodology is to be employed for oral administration, each of the two requisite compositions may be provided individually or in combination in the form of prepared capsules, cachets, or tablets each containing a predetermined quantity of the 13-S-derivative composition and the tetracycline-type antibiotic. Their preparation may also take form as a powder or granules; or dissolved or suspended in a solution or suspension within an aqueous liquid or a nonaqueous liquid; or within an oil-in-water emulsion or conversely within a water-in-oil liquid emulsion for ingestion or for oral cavity lavage treatments. These solid or liquid formulations may generally include one or more carrier materials such as flavoring agents, binders, buffers, diluents, surface active agents, thickeners, lubricants, preservatives, and the like. It is deemed that all of these methods for formulating, preparing, and administering the requisite compositions are conventionally known.

The effective dosages to be employed in-vivo are typically dictated by the intended application or use circumstances; and are generally decided by reconciling several different factors. First, it will be recognized and appreciated that each embodiment of the 13-S-derivative composition and each embodiment of the alternative tetracycline composition (analogue or derivative) will have individual specific pharmacological activity which can be represented and evaluated as the Minimal Inhibitory Concentration (hereinafter "MIC") and as the Minimal Lethal Concentration (hereinafter "MLC")—each of which varies with its specific formulation and chemical structure. Second, any given specific chemical formulation will also have varying MIC and MLC dosages which fluctuate with the cell type—as, for example, with the genus and species of microorganism; thus, the MIC and MLC of each individual composition will vary markedly—as, for example, when administered to gram-positive bacteria in comparison to gram-negative bacteria or to the various different genera of fungi, rickettsia, and parasites. Thirdly, the degree of tetracycline resistance is known to vary substantially among the different cell types, their delineated genera, and among the different species comprising a single genus; this varying degree of tetracycline resistance is without regard to whether the mechanism of resistance is based upon an active efflux system or a ribosome protection system intracellularly. Lastly, each specific route of in-vivo administration is conventionally recognized to require markedly different dose concentrations of conventionally known tetracycline compounds; accordingly, in-vivo therapeutic dosages will vary depending upon whether the tetracycline-type composition is given orally, parenterally, or topically. Each of these individual factors should be taken in consideration by the user when deciding the proper dosage or concentration for both 13-S-derivative composition and the other tetracycline antibiotic composition.

In general, however, it is most desirable that the dosage and concentration of the 13-S-derivative composition (broadly defined by Formulation I) be administered in a subinhibitory quantity—that is, less than the minimum inhibitory concentration or the minimum lethal concentration for that specific composition when employed against a tetracycline-resistant cell. In comparison, it is essential that the chosen alternative tetracycline-type composition (tetracycline analogue or tetracycline derivative meeting the broad definitional requirements of Formula II above) be employed in at least a minimum inhibitory concentrations; and preferably be administered at an effective dosage to provide a minimal lethal concentration in-situ. Accordingly, it is deemed that the concentrations for the two concomitantly administered compositions are conventionally known within the art; and can be optimized with a minimum of difficulty.

In this context, and as empirically demonstrated by the data of Tables E2 and E3 which follow hereinafter, the concomitant administration of the 13-S-derivative composition and the other tetracycline-type composition together provides not only means for overcoming tetracycline resistance but also offers the capability to enhance the pharmacological activity of the known tetracycline-type composition to exert cidal activity and cidal effects upon the cell. Contrary to the universally accepted conventional view that commercially available tetracyclines, regardless of formulation, are only bacteriostatic agents—i.e., agents that do not kill but only inhibit future growth, the present method provides a synergistic combination of compositions which enhances the antibiotic activity of the tetracycline-type composition; and for the first time, allows the enhanced tetracycline-type composition to exert bacteriocidal powers against a broad spectrum of bacteria—i.e., the ability to kill these cells rather than merely inhibit their growth.

In addition, the general molar ratio of 13-S-derivative composition to alternative tetracycline-type composition is expected generally to be from 0.01:100.0, and is preferably in the range from 0.05:2.0. It is most desirable, however, that in no instance should the dosage of the 13-S-derivative composition be employed in a concentration which is within the MIC or MLC values. In comparison, the alternative, tetracycline-type composition (tetracycline or tetracycline analogue or tetracycline derivative) should be administered in accordance with conventional practice for the efficacious therapeutic treatment of infection or disease in humans and/or animals. Accordingly, for therapeutic purposes, the daily dosage of 13-S-derivative composition for treatment of disease in living mammals is expected to lie in the range from 0.01-100 mg/kg of normal body weight while the dosage of the other tetracycline, analogue or derivative, (preferably from 15 to 30 mg/kg) should continue to be given in the range from 500 milligrams to 2.0 grams per day depending upon the age, weight, and route of administration.

It will also be understood that the normal, conventionally known, precautions will be taken regarding the administration of tetracyclines generally in order to ensure their efficacy under normal use circumstances. Especially when employed for therapeutic treatment of humans and animals in-vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

Mode And Manner Of Pharmacological Activity

It must be emphasized again that the present methodology is useful with all cells, regardless of type, source, family, genus, or species which have genetic determinants for tetracycline resistance. The methodology of the present invention is suitable for use with both tetracycline resistance attributable to an active efflux transport system utilizing one or more TET proteins which actively bind with tetracycline-type antibiotics and transport the tetracycline composition out of the cytoplasm of the cell; and also with tetracycline resistance which is a nonefflux system and typically involves a ribosome protection mechanism which causes a tetracycline antibiotic to fail to inhibit protein synthesis intracellularly. Regardless of which tetracycline resistance mechanism is present within the resistant cell, the present methodology is effective in overcoming tetracycline resistance and in rendering the cell tetracycline-sensitive. Although the sequence of molecular reactions remains far from understood at the present time, the concurrent or simultaneous administration of at least one 13-S-derivative composition prepared in accordance with Formula I and at least one other tetracycline antibiotic composition in accordance with Formulation II causes an in-situ conversion of the cell from a resistant state into a tetracycline-sensitive state.

The efficacy and utility of the present methodology is based upon the cell's unexpected preferential reaction with the 13-S-derivative composition which is desirably present in a subinhibitory concentration; and the comparable absence of avidity by the cell for the other tetracycline-type composition concomitantly administered. The resistance mechanism of the cell—be it the active efflux system or the ribosome protection system—focuses upon and interacts with the 13-S-derivative composition primarily and predominantly; the concurrent or simultaneous presence of the other tetracycline-type antibiotic composition is relatively ignored and effectively overlooked by the tetracycline-resistance mechanism of the cell. Consequently, the other tetracycline-type antibiotic composition is allowed to accumulate intracellularly in at least a minimum inhibitory concentration (and preferably in a minimum lethal concentration); and this other tetracycline-type antibiotic is able to bind to the ribosomes and to exert its recognized pharmacological activity intracellularly to prevent further protein synthesis within that cell. In this respect, the administered 13-S-derivative composition of Formula I is clearly the preferred composition for reaction with the tetracycline-resistant mechanism present; and by this preferred reactivity, acts as a blocking agent to engage and to divert the tetracycline resistance mechanism of that cell to the extent that the concurrently or simultaneously administered other tetracycline-type antibiotic composition of Formula II is able to exert its characteristic pharmacological activity efficaciously against the ribosomes of the cell and to prevent further protein synthesis intracellularly. The present methodology is thus effective and useful by the cell's own preference for engagement and reaction with the 13-S-derivative composition rather than with the concomitantly administered other tetracycline-type antibiotic. In this manner, the cumulative effect is to render the cell tetracycline-sensitive for therapeutic purposes.

EXPERIMENTAL STUDIES

The efficacy and utility of the present invention are demonstrated and evidenced by a series of experiments and resulting empirical data as will be described hereinafter. These experiments will serve to better illustrate the essential components of the present methodology; to demonstrate the value of the preferred embodiments comprising 13-S-derivative compositions prepared in accordance with Formula I; and to document the range and diversity of some tetracycline-resistant microorganisms which can be rendered sensitive to tetracycline therapy by employing the present methodology.

For purposes of conducting the experimental model, only tetracycline was employed uniformly in combination with a variety of different 13 substituted mercapto tetracyclines. Nevertheless, it will be understood that tetracycline is employed merely as a representative of all the different compositions and embodiments of tetracyclines, tetracycline analogues, and tetracycline derivatives conforming to the definition of Formula II given previously; and that the present invention is not limited to the use of tetracycline alone as a specific chemical formulation and structure. Moreover, it will be understood that the experiments and empirical data presented hereinafter are merely illustrative examples of the present invention without regard to specific applications or particular uses; and that the described experiments are merely representative of the totality of embodiments encompassed within the scope of the present invention.

Experimental Series 1

Initially, the inhibitory effects of a variety of different 13-S-derivatives in comparison to tetracycline and minocycline were examined using a variety of different bacteria. These included tetracycline sensitive (hereinafter "Tc$^s$") and tetracycline resistant (hereinafter "Tc$^r$") strains of $E.\ coli$, $S.\ aureus$, and $E.\ faecalis$. The general protocol for performing these experiments is as follows: Cultures were grown up fresh in L broth in the morning from an overnight culture. After 4–6 hours of growth, each bacterial culture was diluted to an $A_{530}$ of 0.2–0.5 depending on the strain ($E.\ coli$, 0.5; $S.\ aureus$, 0.4; $E.\ fecaelis$, 0.2). Individual tubes, containing 1 ml of L broth and different concentrations of 13-S-derivatives, were inoculated with the different bacterial cultures and then incubated at 37° C. After 17–18 h of incubation, the concentration of each 13-S-derivative at which no observed cloudiness was seen was called the minimal inhibitory concentration (MIC). The minimal lethal concentration (MLC), i.e., that concentration which kills 99.9%, was based on the number of bacteria initially inoculated into the assay tubes. Those culture tubes showing no bacterial growth after incubation at 37° C. were evaluated for the number of bacteria remaining.

The results obtained in this experimental series are provided by Tables E1–E3 below.

TABLE E1

SUSCEPTIBILITY TESTING OF E. coli

| Drug | Tc$^s$ (ML308-225) MIC (ug) | MLC (ug) | Class A Tc$^r$ (D1-299) MIC (ug) | MLC (ug) | Class B Tc$^r$ (D1-109) MIC (ug) | MLC (ug) |
|---|---|---|---|---|---|---|
| Tetracycline | 0.5 ± 0.25 | 40 ± 0.25 | 150 ± 0.25 | 200 | >200 | >200 |
| Minocycline | <4 | <4 | <4 | 20 | 6 ± 2 | 30 ± 10 |
| Benzyl* | 16 ± 5 | 25 ± 5 | 45 ± 20 | 150 ± 50 | 30 ± 0.25 | 90 ± 10 |
| Cyclohexyl* | 60 ± 10 | 120 | 100 ± 0.25 | >200 | ND | ND |
| Cyclopentyl* | 20 | 50 | 40 ± 0.25 | 80 | 80 ± 40 | 100 ± 50 |
| Propyl* | 30 ± 5 | 50 ± 10 | 40 ± 0.25 | 50 | 50 | 80 |
| Isopropyl* | 22 ± 2 | 50 | 45 ± 5 | 50 | 35 ± 5 | 45 ± 15 |
| Ethyl* | 5 ± 0.25 | 50 | 14 ± 4 | 45 ± 5 | 35 ± 15 | 50 ± 10 |

*Note: ±0.25 indicates that the same MIC or MLC was determined in two or more experiments. Other values represent experimental error determined by averaging the values obtained in multiple experiments. If no value is given, the experiment has not been repeated. Larger numbers will consistently have larger errors since all experiments were done by the standard 1 ml serial dilution liquid MIC procedure.
ND = not done.
Tc$^s$ = tetracycline sensitive strain
Tc$^r$ tetracycline resistant strain
*S-mercapto derivative of methacycline

TABLE E2

SUSCEPTIBILITY TESTING OF S. aureus

| Drug | Tc$^s$ (RN450) MIC (ug) | MLC (ug) | Tc$^r$ (RN4250) MIC (ug) | MLC (ug) |
|---|---|---|---|---|
| Tetracycline | 0.75 ± 0.25 | >6 | 90 ± 10 | 100 |
| Minocycline | <0.25 | 8 | <0.25 | >80 |
| Benzyl | 0.2 ± 0.1 | 10 ± 2 | 1 ± 0.25 | 10 ± 4 |
| Cyclohexyl | 2.5 ± 1.25 | 10 ± 5 | 1.5 ± 0.5 | 10 ± 4 |
| Cyclopentyl | 1 | 5 | 2 ± 0.25 | 6 ± 2 |
| Propyl | 0.5 ± 0.25 | 5 | 4 ± 0.25 | 16 ± 4 |
| Isopropyl | 0.5 ± 0.25 | 6 ± 2 | 4.5 ± 0.5 | 8 |
| Ethyl | 0.5 ± 0.25 | 4 | 5 ± 2 | 30 ± 10 |

Tc$^s$ = tetracycline sensitive strain
Tc$^r$ = tetracycline resistant strain

TABLE E3

SUSCEPTIBILITY TESTING OF E. faecalis

| Drug | Tc$^s$ (ATCC9790r) MIC (ug) | MLC (ug) | Tc$^r$(L) (ATCC9790r/TetL) MIC (ug) | MLC (ug) | Tc$^r$(M) (ATCC09790R/TetM) MIC (ug) | MLC (ug) |
|---|---|---|---|---|---|---|
| Tetracycline | 0.25 | >200 | 90 ± 10 | >300 | 100 | 300 |
| Minocycline | <0.25 | >40 | <0.25 | >80 | 10 | >80 |
| Benzyl | 0.5 ± 0.25 | 8 ± 0.25 | 0.75 ± 0.25 | 8 ± 2 | 3.5 ± 1 | 18 ± 2 |
| Cyclohexyl | 1.25 ± 0.25 | 8 | 1.5 ± 0.5 | 8 ± 2 | 2.5 ± 0.5 | 10 ± 0.25 |
| Cyclopentyl | 1 ± 0.25 | 10 ± 4 | 1 ± 0.5 | 18 ± 2 | 3 ± 1 | >16 |
| Propyl | 1.5 ± 0.25 | 40 ± 0.25 | 2.5 ± 0.5 | 60 ± 10 | 16 ± 2 | 30 ± 10 |
| Isopropyl | 3 ± 1 | 20 ± 0.25 | 3 ± 1 | 100 ± 0.25 | 22 ± 2 | >200 |
| Ethyl | 1 ± 0.5 | 40 ± 0.25 | 4 ± 1 | 100 ± 0.25 | 25 ± 5 | >200 |

Tc$^s$ = tetracycline-sensitive strain
Tc$^r$ = tetracycline-resistant strain

A close inspection and reading of Tables E1-E3 will reveal the following points regarding the tetracycline susceptible strains and the tetracycline resistant strains tested. These are:

Susceptible Strains

1. E. coli (Table E1, Column 1)

None of these compounds was more active than tetracycline or minocycline against susceptible E. coli strains. The most active was the ethyl-S-derivative which showed an MIC of 5 ug/ml.

2. S. aureus (Table E2, Column 1)

Against susceptible S. aureus, all of the 13-S-derivatives were effective alone within therapeutic ranges. They were about as active as tetracycline and minocycline (except perhaps the cyclohexyl derivative). All 13-S-derivatives showed bacteriocidal activity better than tetracycline or minocycline of which 4 showed bacteriocidal activity at a level of about 5 ug/ml.

3. E. faecalis (Table E3, Column 1)

Against susceptible Enterococcus faecalis, all the tested compositions were effective well within a therapeutic range and all, but the isopropyl derivative, at 1 ug/ml or less. All showed greater bacteriocidal activity than did tetracycline or minocycline, especially the benzyl, cyclohexyl, and cyclopentyl S-derivatives.

Resistant Strains

1. All the other compositions were more active than tetracycline against resistant E. coli strains (both Class A and Class B determinants). None individually was as active as minocycline. Most 13-S-derivatives showed bacteriocidal activity lower than tetracycline against resistant E. coli, but not within therapeutic ranges (Table E1, Columns 2 and 3).

2. Against resistant S. aureus, all the tested compounds showed an MIC within a therapeutic range, at least 20-100 fold more active than tetracycline. None individually was as active as minocycline. All 13-S-derivatives were more bacteriocidal than tetracycline or minocycline alone with cyclopentyl showing an MLC of 6±2 ug/ml. Benzyl, cyclohexyl, and cyclopentyl S-derivatives each showed similar MIC values and MLC values against susceptible and resistant S. aureus. The most active 13-S-derivative was the cyclopentyl form (Table E2, Column 2).

3. All the tested compositions had an MIC within a therapeutic range against E. faecalis bearing the Tet L determinant: benzyl>cyclopentyl>cyclohexyl, followed by the others. The 13-S-derivatives were equally effective by MIC against susceptible and Tet L containing Enterococcus. All were more bacteriocidal than tetracycline and minocycline individually; the MLC for benzyl and cyclohexyl was 8±2 ug/ml (Table E3, Column 2).

4. Against Tet M containing *E. faecalis*, all the other tested compounds were considerably more antibacterial than tetracycline. Three of them, the benzyl, cyclohexyl, and cyclopentyl derivatives also had MIC values below minocycline and within therapeutic levels (Table E3, Column 3). Bacteriocidal activity was observed, but above therapeutic levels.

5. While the MLC against resistant *S. aureus* and *E. faecalis* was 8-10 ug/ml for the most active drugs, a killing effect (seen as a 10-99% drop in cell viability) by the analogues occurred at considerably lower drug concentrations (see charts).

Experimental Series 2

Subsequently, another series of experiments was conducted which employed concurrent administrations of tetracycline and at least one other 13-S-derivative composition in accordance with Formula I above. The general experimental protocol for synergy studies followed substantially that procedure employed for the standard MIC and MLC assays. The organisms were grown in fresh L broth and inoculated in culture tubes containing different concentrations of 13-S-derivative compositions and tetracycline together.

The previously described methods for determining MIC and MLC were otherwise followed.

Accordingly, the results are provided by Charts 1-5 in which: Chart 1 represents the concurrent administration of 13-cyclopentyl sulfide derivative of methacycline in varying proportional ratios to tetracycline; Chart 2 represents 13-propyl-sulfide derivatives of methacycline in varying proportional ratios with tetracycline; Chart 3 represents varying proportional ratios of 13-cyclohexyl-sulfide derivatives of methacycline and tetracycline administered concurrently; Chart 4 represents varying proportional ratios of 13-benzylsulfide derivatives of methacycline delivered concurrently with tetracycline; and Chart 5 illustrates the concurrent administration of varying proportions of 13-ethyl-sulfide derivatives of methacycline and tetracycline.

Chart 1: MIC/MLC (ug/ml) dosages for tetracycline-resistant strains using cyclopentyl-sulfide derivatives of methacycline with and without tetracycline Strain: *E. coli* (D1-299)

| Tc\A | 0 | 4 | 8 | 16 | 32 |
|---|---|---|---|---|---|
| 0 | | | | | |
| 2 | | | | + | ↓ |
| 4 | | | 0 | 0 | |
| 8 | | | ↓ | | |
| 16 | | | ↓ | | |

-continued
Chart 1: MIC/MLC (ug/ml) dosages for tetracycline-resistant strains using cyclopentyl-sulfide derivatives of methacycline with and without tetracycline Strain: *S. aureus* (RN4250)

| Tc\A | 0 | 1 | 2 | 4 | 8 |
|---|---|---|---|---|---|
| 0 | | | 0 | ↓ | |
| 1 | | + | ↓ | | |
| 2 | | + | ↓ | | |
| 4 | | 0 | ↓ | | |
| 8 | | 0 | ↓ | | |

Strain: *E. faecalis* (Tet L)

| Tc\A | 0 | 1 | 2 | 4 | 8 |
|---|---|---|---|---|---|
| 0 | | 0 | ↓ | ↓ | ↓ |
| 1 | | 0 | ↓ | ↓ | ↓ |
| 2 | | 0 | ↓ | ↓ | ↓ |
| 4 | | 0 | ↓ | ↓ | ↓ |
| 8 | | 0 | ↓ | ↓ | ↓ |

Strain: *E. faecalis* (Tet M)

| Tc\A | 0 | 2 | 4 | 8 | 16 |
|---|---|---|---|---|---|
| 0 | | | 0 | ↓ | ↓ |
| 2 | | | 0 | 0 | ↓ |
| 4 | | | 0 | 0 | ↓ |
| 8 | | | 0 | ↓ | ↓ |
| 16 | | | 0 | ↓ | ↓ |

Note:
 Growth;
 0 No Growth (MIC);
 ↓ Killing;
 □ 99.9% Killing (MLC).

Tc = tetracycline concentration (ug/ml).
A = 6-deoxy-13-(cyclopentyl mercapto) tetracycline concentration (ug/ml)

Chart 2: MIC/MLC (ug/ml) dosages for tetracycline-resistant strains using propyl-sulfide derivatives of methacycline with and without tetracycline Strain: E. coli (D1-299)

| Tc\B | 0 | 4 | 8 | 16 | 32 |
|---|---|---|---|---|---|
| 0 |  |  |  |  | 0 |
| 4 |  |  | 0 | ↓ |  |
| 8 |  | ↓ | ↓ |  |  |
| 16 |  |  |  |  |  |
| 32 |  |  |  |  |  |

Strain: S. aureus (RN4250)

| Tc\B | 0 | 2 | 4 | 8 | 16 |
|---|---|---|---|---|---|
| 0 |  |  | ↓ | ↓ | ↓ |
| 2 |  | + | ↓ | ↓ | ↓ |
| 4 |  | 0 | ↓ | ↓ | ↓ |
| 8 |  | 0 | ↓ | ↓ | ↓ |
| 16 |  |  | ↓ | ↓ | ↓ |

Strain: E. faecalis (Tet L)

| Tc\B | 0 | 2 | 4 | 8 | 16 |
|---|---|---|---|---|---|
| 0 |  | 0 | 0 | ↓ | ↓ |
| 2 |  | 0 | 0 | ↓ | ↓ |
| 4 |  | 0 | 0 | ↓ | ↓ |
| 8 |  | 0 | ↓ | ↓ | ↓ |
| 16 |  | ↓ | ↓ | ↓ | ↓ |

-continued
Chart 2: MIC/MLC (ug/ml) dosages for tetracycline-resistant strains using propyl-sulfide derivatives of methacycline with and without tetracycline Strain: E. faecalis (Tet M)

| Tc\B | 0 | 4 | 8 | 16 | 32 |
|---|---|---|---|---|---|
| 0 |  |  |  | ↓ | ↓ |
| 4 |  |  |  | ↓ | ↓ |
| 8 |  |  | + | ↓ | ↓ |
| 16 |  |  | 0 | ↓ | ↓ |
| 32 |  |  | 0 | ↓ | ↓ |

Note:

Growth;

0 No Growth (MIC);

↓ Killing;

☐ 99.9% Killing (MLC).

Tc = tetracycline concentration (ug/ml).

B = 6-deoxy-13-(propyl mercapto) tetracycline concentration (ug/ml)

Chart 3: MIC/MLC (ug/ml) dosages for tetracycline-resistant strains using cyclohexyl-sulfide derivatives of methacycline with and without tetracylcine Strain: E. coli (D1-299)

| Tc\C | 0 | 5 | 10 | 20 | 40 |
|---|---|---|---|---|---|
| 0 | ++++ | ++++ | ++++ | ++++ | ++++ |
| 2.5 | ++++ | ++++ | + | ↓ | ↓ |
| 5 | ++++ | 0 | ↓ |  |  |
| 10 | ++++ | ↓ | ↓ |  |  |
| 20 | ++++ | ↓ |  |  |  |

-continued
Chart 3: MIC/MLC (ug/ml) dosages for tetracycline-resistant strains using cyclohexyl-sulfide derivatives of methacycline with and without tetracylcine Strain: *S. aureus* (RN4250)

| Tc\C | 0 | 1 | 2 | 4 | 8 |
|---|---|---|---|---|---|
| 0 | ++++ | ↓ | | | |
| 1 | ++++ | ↓ | | | |
| 2 | ++++ | ↓ | | | |
| 4 | ++++ | | | | |
| 8 | ++++ | | | | |

Strain: *E. faecalis* (Tet L)

| Tc\C | 0 | 1 | 2 | 4 | 8 |
|---|---|---|---|---|---|
| 0 | ++++ | 0 | ↓ | ↓ | ↓ |
| 1 | ++++ | 0 | ↓ | ↓ | |
| 2 | ++++ | 0 | ↓ | ↓ | |
| 4 | ++++ | 0 | ↓ | ↓ | |
| 8 | ++++ | 0 | ↓ | | |

Strain: *E. faecalis* (Tet M)

| Tc\C | 0 | 2.5 | 5 | 10 | 20 |
|---|---|---|---|---|---|
| 0 | ++++ | 0 | ↓ | | |
| 2.5 | ++++ | 0 | ↓ | | |
| 5 | ++++ | 0 | ↓ | | |
| 10 | ++++ | 0 | ↓ | ↓ | |
| 20 | ++++ | 0 | ↓ | ↓ | ↓ |

Note:
++++ Growth;
0 No Growth (MIC);
↓ Killing;
□ 99.9% Killing (MLC).

Tc = tetracylcine concentration (ug/ml).
C = 6-deoxy-13-(cyclohexyl mercapto) tetracycline concentration (ug/ml)

Chart 4: MIC/MLC (ug/ml) dosages for tetracycline-resistant strains using benzyl-sulfide derivatives of methacycline with and without tetracylcine Strain: *E. coli* (D1-299)

| Tc\D | 0 | 4 | 8 | 16 | 32 |
|---|---|---|---|---|---|
| 0 | ++++ | ++++ | ++++ | + | ↓ |
| 4 | ++++ | ++++ | ↓ | ↓ | |
| 8 | ++++ | +++ | ↓ | ↓ | |
| 16 | ++++ | ↓ | ↓ | ↓ | |
| 32 | ++++ | ↓ | ↓ | | |

Strain: *S. aureus* (RN4250)

| Tc\D | 0 | 1 | 2 | 4 | 8 |
|---|---|---|---|---|---|
| 0 | ++++ | ↓ | ↓ | ↓ | ↓ |
| 1 | ++++ | ↓ | ↓ | ↓ | |
| 2 | ++++ | ↓ | ↓ | | |
| 4 | ++++ | ↓ | | | |
| 8 | ++++ | ↓ | | | |

Strain: *E. faecalis* (Tet L)

| Tc\D | 0 | 1 | 2 | 4 | 8 |
|---|---|---|---|---|---|
| 0 | ++++ | ↓ | ↓ | ↓ | ↓ |
| 1 | ++++ | ↓ | ↓ | ↓ | ↓ |
| 2 | ++++ | ↓ | ↓ | ↓ | ↓ |
| 4 | ++++ | ↓ | ↓ | ↓ | ↓ |
| 8 | ++++ | ↓ | ↓ | | |

-continued
Chart 4: MIC/MLC (ug/ml) dosages for tetracycline-resistant strains using benzyl-sulfide derivatives of methacycline with and without tetracylcine

*E. faecalis* (Tet M)

| Tc\D | 0 | 2 | 4 | 8 | 16 |
|---|---|---|---|---|---|
| 0 | ++++ | 0 | ↓ | ↓ | ↓ |
| 2 | ++++ | 0 | ↓ | ↓ | ↓ |
| 4 | ++++ | 0 | ↓ | ↓ | ↓ |
| 8 | ++++ | ↓ | ↓ | ↓ | ↓ |
| 16 | ++++ | ↓ | ↓ | ↓ | ↓ |

Note:

++++ Growth;

0 No Growth (MIC);

↓ Killing;

 99.9% Killing (MLC).

Tc = tetracylcine concentration (ug/ml).

D = 6-deoxy-13-(benzyl mercapto) tetracycline concentration (ug/ml)

Chart 5: MIC/MLC (ug/ml) dosages for tetracycline-resistant strains using ethyl-sulfide derivatives of methacycline with and without tetracylcine Strain: *E. coli* (D1-299)

| Tc\E | 0 | 2 | 4 | 8 | 16 |
|---|---|---|---|---|---|
| 0 | ++++ | ++++ | ++++ | ++ | 0 |
| 2 | ++++ | ++++ | +++ | 0 | ↓ |
| 4 | ++++ | ++ | 0 | ↓ | ↓ |
| 8 | ++++ | ++ | ↓ | ↓ | |
| 16 | ++++ | ↓ | ↓ | ↓ | |

-continued
Chart 5: MIC/MLC (ug/ml) dosages for tetracycline-resistant strains using ethyl-sulfide derivatives of methacycline with and without tetracylcine Strain: *S. aureus* (RN4250)

| Tc\ | | | | | |
|---|---|---|---|---|---|
| | | | | | |
| | | | | | |
| | | | | | |
| | | | | | |
| | | | | | |
| | | | | | |

Strain: *E. faecalis* (Tet L)

| Tc\ | | | | | |
|---|---|---|---|---|---|
| | | | | | |
| | | | | | |
| | | | | | |
| | | | | | |
| | | | | | |
| | | | | | |

Strain: *E. faecalis* (Tet M)

| Tc\ | | | | | |
|---|---|---|---|---|---|
| | | | | | |
| | | | | | |
| | | | | | |
| | | | | | |
| | | | | | |
| | | | | | |

Note:

++++ Growth;

0 No Growth (MIC);

↓ Killing;

 99.9% Killing (MLC).

Tc = tetracycline concentration (ug/ml).

E = 6-deoxy-13-(ethyl mercapto) tetracycline concentration (ug/ml)

As evidenced by the data of Charts 1-5, the results of administering 13-S-derivative tetracycline compositions concurrent with varying proportional ratios of tetracycline clearly support the following conclusions:

1. Against the tetracycline resistant (Class A) *E. coli* (strain D1-299) synergy was observed. The most effective analogues were cyclopentyl, cyclohexyl, and ethyl. These all inhibited growth at concentrations of 5 ug/ml or less of analogue and tetracycline. Synergy was also demonstrated in bacteriocidal activity, although the amounts of the 13-S-derivatives needed were higher than 5 ug/ml in order to kill 99.9% of the cells with 4-5 ug/ml of tetracycline.

2. Against tetracycline resistant *S. aureus*, all the 13-S-derivatives tested showed synergistic activity at levels of both drugs below 4 ug/ml. In addition, cyclohexyl>cyclopentyl>benzyl showed bacteriocidal activity within therapeutic combinations with tetracycline where the combined dose of the two drugs was ≦6 ug/ml to achieve MLC.

3. Against *E. faecalis* (Tet L), all four 13-S-derivatives showed excellent synergy in inhibiting growth in combination: <1 ug/ml of analogue with 1 ug/ml tetracycline. While bacteriocidal effects were seen synergistically, the amounts of drugs needed to produce the MLC were higher than each at 4-5 ug/ml.

4. Against *E. faecalis* (Class M) cyclopentyl, cyclohexyl, and benzyl S-derivatives showed little, if any synergistic activity with tetracycline. However, the propyl-S-derivative, while not as active alone, did show meaningful synergy.

Summary

1. These studies show that a group of S-alkyl substitutions and the benzyl substitution at the 13th carbon position of methacycline can inhibit growth of both susceptible and tetracycline resistant gram-positive (and to a less extent gram-negative) organisms.

2. In combination with tetracycline, all of these 13-S-derivatives show synergy, both in growth inhibition and in bacteriocidal activity for gram-positive as well as gram-negative susceptible and resistant strains.

3. All of the 13-S-derivatives tested show bacteriocidal activity, although this is most evident against the gram-positive bacteria tested alone and in synergy with tetracycline, and against *E. coli* in synergy with tetracycline.

4. All the 13-S-derivatives tested alone show greater bacteriocidal activity than minocycline against *S. aureus* and *E. faecalis*, chiefly the benzyl, cyclohexyl, and cyclopentyl derivatives.

The present invention is not to be restricted in form nor limited in scope except by the claims appended hereto.

What I claim is:

1. A method for therapeutically treating a tetracycline resistant cell with tetracycline, said method comprising the steps of:
    administering to the cell a predeterminable quantity of at least a first composition selected from the group consisting of 6-deoxy-13-(substituted mercapto) tetracyclines; and
    concomitantly administering to the cell a predeterminable quantity of at least a second composition selected from the chemical class consisting of tetracyclines, tetracycline analogues and tetracycline derivatives which are not 6-deoxy-3-(substituted mercapto) tetracyclines.

2. A method for altering a cell from a tetracycline-resistant state into a tetracycline-sensitive state, said method comprising the steps of:
    administering to the cell a predeterminable quantity of at least a first composition selected from the chemical class consisting of 6-deoxy-13-(substituted mercapto) tetracyclines; and
    concomitantly administering to the cell a predeterminable quantity of at least a second composition selected from the chemical class consisting of tetracyclines, tetracycline analogues and tetracycline derivatives which are not 6-deoxy-13-(substituted mercapto) tetracyclines.

3. A method for exerting cidal tetracycline antibiotic activity against tetracycline resistant cells, said method comprising the steps of:
    administering to the cell a predeterminable quantity of at least a first composition selected from the chemical class consisting of 6-deoxy-13-(substituted mercapto) tetracyclines; and
    concomitantly administering to the cell a predeterminable quantity of at least a second composition selected from the chemical class consisting of tetracyclines, tetracycline analogues, and tetracycline derivatives which are not 6-deoxy-13-(substituted mercapto)tetracyclines.

4. The method as recited in claims 1, 2, or 3 wherein said first composition is a 6-deoxy-13-(alkyl substituted mercapto)tetracycline.

5. The method as recited in claims 1, 2, or 3 wherein said first composition is a 6-deoxy-13-(aryl substituted mercapto)tetracycline.

6. The method as recited in claims 1, 2, or 3 wherein said second composition is tetracycline.

7. The method as recited in claims 1, 2, or 3 wherein said second composition is selected from the group consisting of minocycline, doxycycline, methacycline, demeclocycline, oxytetracycline, and chlortetracycline.

8. The method as recited in claims 1, 2, or 3 wherein said first and second compositions are administered orally.

9. The method as recited in claims 1, 2, or 3 wherein said first and second compositions are administered parenterally.

10. The method as recited in claims 1, 2, or 3 wherein said first and second compositions are administered topically.

11. A method for therapeutically treating a tetracycline resistant cell with a tetracycline analogue, said method comprising the steps of:
    administering to the cell a predeterminable quantity of at least a first composition selected from the chemical class consisting of 6-deoxy-13-(substituted mercapto) tetracyclines; and
    concomitantly administering to the cell a predeterminable quantity of at least a second composition comprising minocycline.

12. A class of 6-deoxy-13-(substituted mercapto)tetracycline compositions useful in the therapeutic treatment of a tetracycline resistant cell in combination with othe classes of tetracyclines, tetracycline analogues and tetracycline derivatives, said class of compositions having the formula

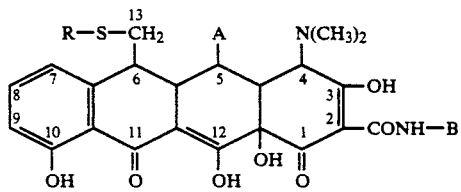
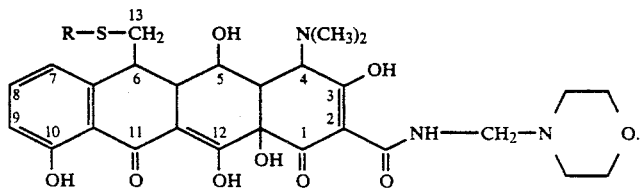
wherein A is selected from the group consisting of hydrogen and a hydroxyl group,
B comprises a morpholine group, and
R is selected from the group consisting of organic entities comprising 1-12 carbon atoms and optionally including heteroatoms.
13. The tetracycline composition as recited in claim 12 having the formula
* * * * *